United States Patent [19]

Krief et al.

[11] Patent Number: 4,996,349

[45] Date of Patent: Feb. 26, 1991

[54] ENANTIOSELECTIVE PROCESS

[75] Inventors: Alain Krief, Wepion; Willy Dumont, Salet, both of Belgium

[73] Assignee: Roussel Uclaf, Paris, France

[21] Appl. No.: 482,647

[22] Filed: Feb. 21, 1990

Related U.S. Application Data

[63] Continuation of Ser. No. 235,093, Aug. 22, 1988, abandoned.

[30] Foreign Application Priority Data

Aug. 24, 1987 [FR] France ................... 87 11849

[51] Int. Cl.$^5$ ............................................. C07C 69/74
[52] U.S. Cl. .................................. 560/124; 562/506; 549/450; 549/454
[58] Field of Search .................. 560/124; 562/506

[56] References Cited

FOREIGN PATENT DOCUMENTS 3229537  2/1984  Fed. Rep. of Germany ...... 560/124

OTHER PUBLICATIONS

Agnew, Chem, Int. Ed. Engl., 22, pp. 63-64 (1983).
Agnew, Chem. 95, p. 60 (1983).
Jurczak, Tetrahedron Report Number 195, pp. 447-488 (1985).

Primary Examiner—Michael L. Shippen
Attorney, Agent, or Firm—Bierman and Muserlian

[57] ABSTRACT

An enantioselective process for the preparation of hemicaronic aldehyde with a cis or trans structure and novel intermediates.

5 Claims, No Drawings

ENANTIOSELECTIVE PROCESS

PRIOR APPLICATION

This application is a continuation of U.S. patent application Ser. No. 235,093 filed Aug. 22, 1988, now abandoned.

OBJECTS OF THE INVENTION

It is an object of the invention to provide a novel process for enantioselective production of hemicaronic aldehydes of cis or trans structure.

It is another object of the invention to provide novel intermediates formed in the said process.

These and other objects and advantages of the invention will become obvious from the following detailed description.

THE INVENTION

The novel process of the invention for the preparation of racemates or optically active isomers of a compound of the formula

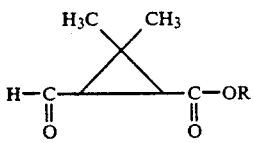

with cis or trans structure wherein R is selected from the group consisting of hydrogen, alkyl of 1 to 4 carbon atoms and aryl of 6 to 12 carbon atoms comprises reacting a diester of the formula

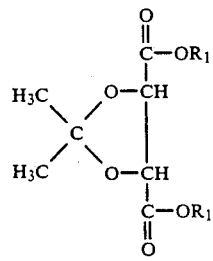

in racemic form or as resolved isomers wherein $R_1$ is selected from the group consisting of alkyl of 1 to 4 carbon atoms, aryl of 6 to 12 carbon atoms and aralkyl of 7 to 8 carbon atoms with a reducing agent to obtain a precursor of a compound of the formula

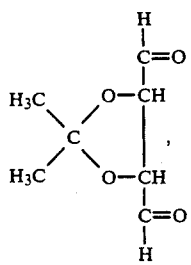

reacting the latter with a Witting-Emmons-Horner reagent of the formula

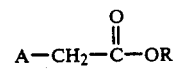

wherein R has the above definition and A is an organic phosphorus to obtain a compound of the formula

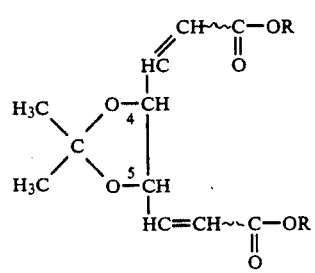

wherein R is as defined above and the wavy lines indicate the cis or trans configuration, reacting the latter with a gem-dimethyl cyclopropanation reagent to obtain a compound of the formula

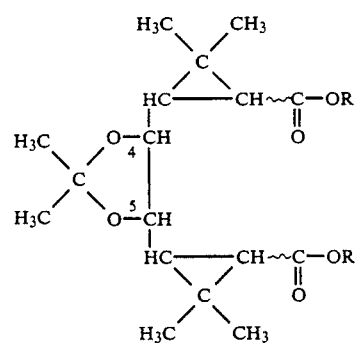

or a compound of the formula

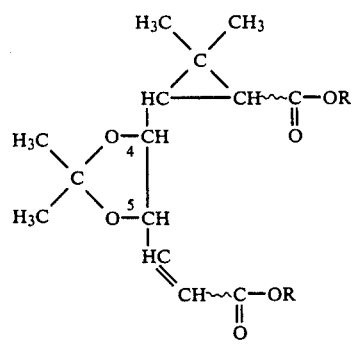

wherein R and the wavy lines have the above definitions which compound Va is optionally reacted with a gem-dimethyl propanation agent to obtain the compound of formula V, the product of formula V or Va is either subjected to hydrolysis of the dioxolane group to obtain a compound respectively of the formula

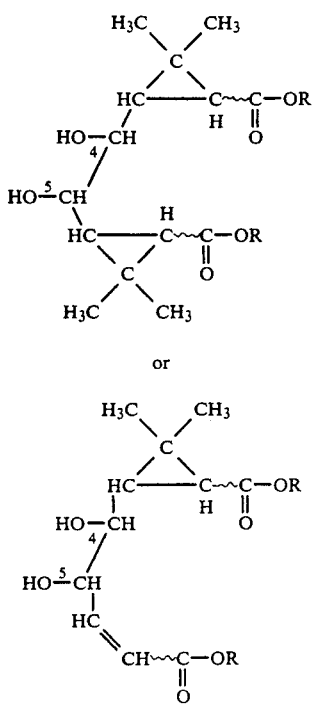

wherein R and the weavy lines have the above definitions and then cleaving the 4,5-bond to obtain a compound of formula I or simultaneously hydrolyzing the dioxolane group and cleaving the 4,5-bond to obtain the compound of formula I.

Examples of R and $R_1$ as alkyl of 1 to 4 carbon atoms are methyl, ethyl, n-propyl, isopropyl and n-butyl and branched butyls. Examples of $R_1$ as aryl are phenyl, tolyl and naphthyl. Examples of $R_1$ as aralkyl are benzyl and phenethyl. A is the organic phosphorus remainder of a Wittig, Emmons or Horner reactant such as a phosphonate, a triarylphosphonium salt or diarylphosphine oxide.

In a preferred mode of the process of the invention, the reducing agent is diisobutylaluminum hydride and the Wittig, Emmons or Horner reagent has the formula

wherein R has the above definition, Alk is alkyl of 1 to 4 carbon atoms and φ is phenyl. The gem-dimethyl cyclopropanation reagent is a compound of the formula

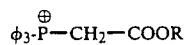

wherein
X is =P(Ar)₃, =S(Ar)₂ or

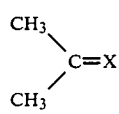

Ar is aryl, preferably phenyl and $R_2$ is hydrogen or alkyl of 1 to 4 carbon atoms.

The acid hydrolysis reagent of the dioxolane group is an organic or inorganic acid such as hydrochloric acid, sulfuric acid, acetic acid, perchloric acid or p-toluene sulfonic acid. The cleavage of the 4,5-bond may be effected with an oxidizing agent such as a periodate, lead tetraacetate or potassium permanganate. For simultaneous hydrolysis and cleavage, the oxidizing agent is preferably periodic acid or periodate in the presence of sulfuric acid.

The reaction of a gem-dimethyl cyclopropanation agent with a compound of formula IV leads to, depending upon the amount of reactant used, a dicyclopropane compound of formula V or a monocyclopropane compound of formula Va which may be reacted to form a compound of formula V.

A preferred process of the invention for the preparation of racemic or optically active isomers of a compound of the formula

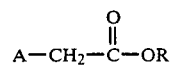

with a trans structure wherein R has the above definition comprises reacting the compound of formula II in racemic or resolved isomeric form with a reducing agent to obtain a precursor of the compound of formula III with the corresponding isomeric structure and reacting the latter with a compound of the formula $$A-CH_2-\overset{O}{\underset{\|}{C}}-OR$$

wherein A and R have the above definition to obtain a compound of the formula

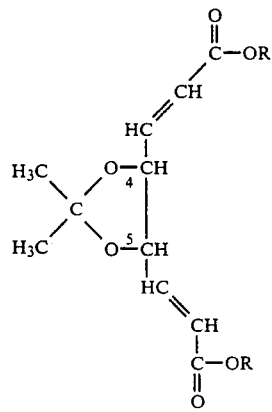

with the geometry of the double bond being trans, subjecting the latter to a gem-dimethyl cyclopropanation agent to obtain a compound of the formula

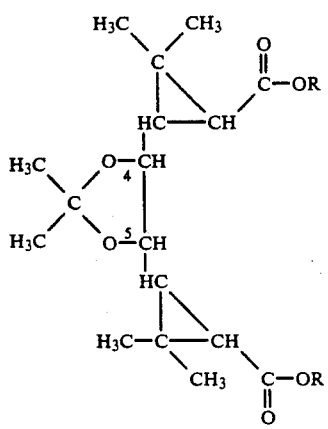

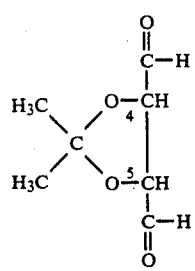

with (4R, 5R) configuration, reacting the latter with a compound of the formula $$A-CH_2-\overset{O}{\underset{\|}{C}}-OR$$

wherein A and R have the above definition to obtain a compound of the formula

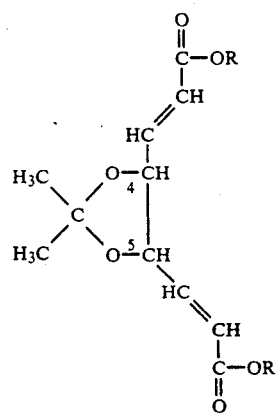

wherein the cyclopropane ring configuration is trans and either hydrolyzing the dioxolane of the latter to obtain a compound of the formula

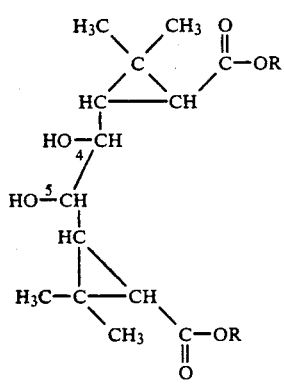

wherein the cyclopropane ring configuration is trans and cleaving the 4,5-bond to obtain a compound of formula $I_4$ or simultaneously hydrolyzing the dioxolane and cleaving the 4,5-bond to obtain a compound of formula $I_4$.

A more preferred process for the preparation of a compound of formula $I_4$ with a 1R, trans configuration comprises reacting the compound of the formula

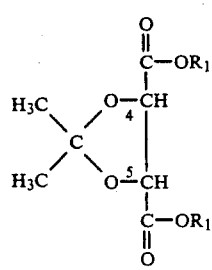

of (4R, 5R) configuration and $R_1$ has the above definition with diisobutylaluminum hydride to obtain a corresponding precursor of compound of the formula with (4S, 5S) configuration and the double bond geometry is trans, reacting the latter with isopropylidene triphenylphosphorane to obtain a compound of the formula

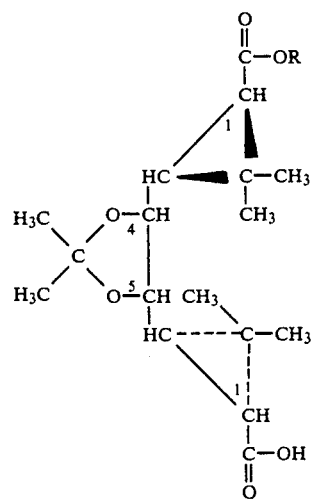

with the (4, 5S) configuration and (1R, trans) configuration on the cyclopropane ring and either subjecting the latter to hydrolysis of the dioxolane to obtain a compound of the formula

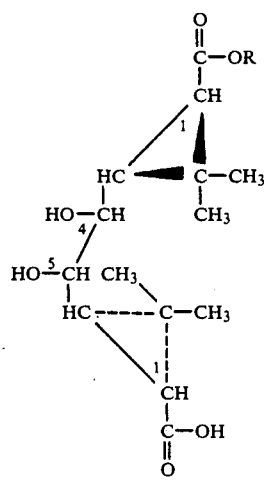 VI'₁ with (4S, 5S) and (1R, trans) configuration on the cyclopropane ring an cleaving the 4,5-bond with an oxidation agent to obtain the compound of formula $I_A$ with (1R, trans) configuration or simultaneously hydrolyzing the dioxolane group and cleaving the 4,5-bond to form a compound of formula $I_A$ with a (1R, trans) configuration.

Another variation of the process of the invention for the preparation of a racemate or optical isomer of a compound of the formula

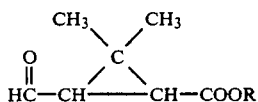 $I_B$ of cis structure and R has the above definition comprises reacting a compound of formula II in racemic or resolved isomeric form with a reducing agent to obtain a precursor of a compound of formula III with a corresponding isomeric structure, reacting the latter with a compound of the formula

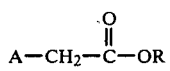

wherein A and R have the above definition to obtain a compound of the formula

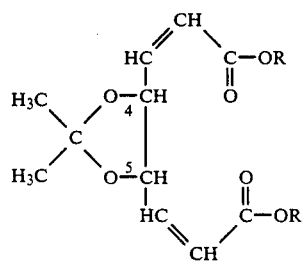 IV"

wherein the double bond has cis geometry, reacting the latter with isopropylidene diphenylsulfurane to obtain a compound of the formula

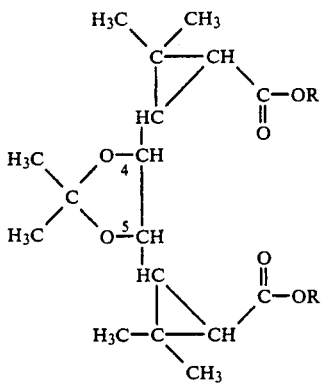 V"

with a cis configuration of the cyclopropane ring and either hydrolyzing the dioxolane group to obtain a compound of the formula

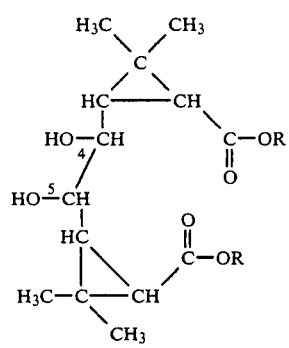 VI"

of cis configuration and cleaving the 4,5-bond to obtain the corresponding compound of formula $I_B$ or simultaneously hydrolyzing the dioxolane group and cleaving the 4,5-bond to obtain the compound of formula $I_B$.

A preferred mode of the said process for the preparation of a compound of formula $I_B$ with a 1R, cis configuration comprises reacting a compound of the formula

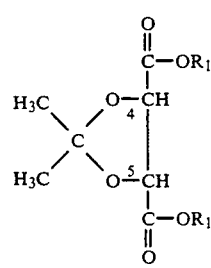 II₁ with (4R, 5R) configuration and R₁ has the above definition with diisobutylaluminum hydride to obtain a corresponding precursor of a compound of the formula

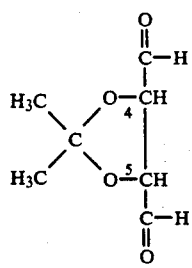

with (4R, 5R) configuration, reacting the latter with a compound of the formula

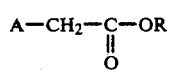

wherein A and R have the above definition to obtain a compound of the formula

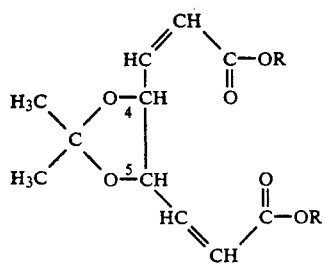

with (4S, 5S) configuration and the double bond geometry is cis, reacting the latter with isopropylidene diphenylsulfurane to obtain a compound of the formula

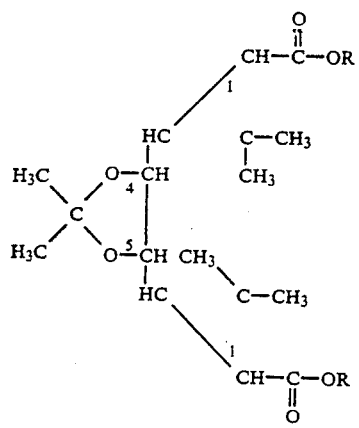

with (4S, 5S) configuration and (1R, cis) configuration on the cyclopropane ring and either hydrolyzing the dioxolane group to obtain a compound of the formula

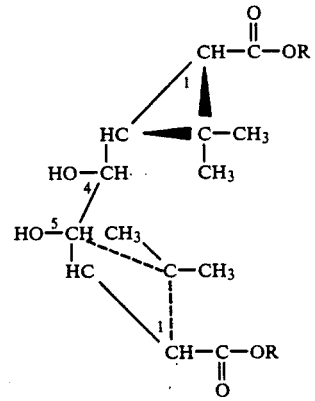

with (4S, 5S) configuration and (1R, cis) configuration on the cyclopropane ring and cleaving the 4,5-bond with an oxidizing agent to obtain a compound of formula $I_B$ with (1R, cis) configuration or simultaneously hydrolyzing the dioxolane group and cleaving the 4,5-bond to obtain a compound of formula $I_B$ with (1R, cis) configuration.

Besides the compounds of formula I with 1R, trans and 1R, cis structure depending on the configuration on the 4,5-position of the starting compound of formula II and the double bond configuration of the compound of formula IV issued from the reaction with A—CH$_2$—COOR, the process of the invention leads to enantioselective access to all possible isomers of formula I.

In the following table, there are represented the configurations of the compounds of formula I with the cis geometry or trans geometry obtained as well as the isolated intermediates starting from the chiral compounds of formula II.

TABLE

| Isomer | X of reactive cyclopropanation | Compound (ii) | | Compound (IV) | | | | Compound (Va) | | | | | Compound (V) | | | | | | Compound (I) |
|---|---|---|---|---|---|---|---|---|---|---|---|---|---|---|---|---|---|---|---|
| | | 4 | 5 | 2 | 4 | 5 | 6 | 2 | 3 | 4 | 5 | 6 | 2 | 3 | 4 | 5 | 6 | 7 | |
| 1 | PΦ$_3$ | R | R | E | S | S | E | R | R | S | S | E | R | R | S | S | R | R | 1R trans |
| 2 | PΦ$_3$ | R | R | Z | S | S | Z | S | S | S | S | E | S | S | S | S | R | R | dl trans |
| 3 | SΦ$_2$ | R | R | Z | S | S | Z | S | S | S | S | Z | S | S | S | S | S | S | 1S trans |
| 4 | PΦ$_3$ ou | R | R | E | S | S | Z | S | S | S | S | E | S | S | S | S | R | R | dl trans |
| 5 | PΦ$_3$ | S | S | E | R | R | E | S | S | R | R | E | S | S | R | R | S | S | 1S trans |
| 6 | PΦ$_3$ | S | S | Z | R | R | Z | R | R | R | R | E | R | R | R | R | S | S | dl trans |
| 7 | SΦ$_2$ | S | S | Z | R | R | Z | R | R | R | R | Z | R | R | R | R | R | R | 1R trans |
| 8 | PΦ$_3$ or | S | S | E | R | R | E | R | R | R | R | E | R | R | R | R | S | S | dl trans |
| 1 | SΦ$_2$ | R | R | Z | S | S | Z | R | S | S | S | Z | R | S | S | S | S | R | 1R cis |
| 5 | SΦ$_2$ | S | S | Z | R | R | Z | S | R | R | R | Z | S | R | R | R | R | S | 1S cis |

The compounds of formulae IV, V, Va, VI and VIa are new and are also an object of the invention to prepare the compounds of formula I with a cis structure. The compound obtained from reduction of the compound of formula II$_1$ with diisobutyl aluminium hydride is new and is also an object of the invention.

The compounds of formula I are known as intermediates useful for the synthesis of chrysantemic acid and its analogs, especially the halogenated analogs. The esters of formula II are known and can be prepared from tartaric acid as described in the Examples.

In the following examples there are several preferred embodiments to illustrate the invention. However, it should be understood that the invention is not intended to be limited to the specific embodiments.

EXAMPLE 1

Methyl (1R,3R) 3-formyl-2,2-dimethyl-cyclopropane carboxylate

STEP A: Methyl (4R,5R) 2,2-dimethyl-1,3-dioxolane-4,5-dicarboxylate

A solution of 0.2 g of p-toluene sulfonic acid in 20 ml of methanol was added to a solution of 50.5 g of (2R,3R) tartaric acid in 80 g of 2,2-dimethoxy-propane and the mixture was refluxed for 15 hours. After the addition of 40 g of 2,2-dimethoxy-propane in 225 ml of cyclohexane, the mixture was slowly distilled for 24 hours at 79° C. 0.5 g of potassium carbonate were added and then the rest of the cyclohexane was evaporated. The residue was purified by fractional distillation to obtain 67 g of the expected product boiling at 86° to 91° C. at 0.4 mm Hg.

IR Spectrum (cm$^{-1}$):
3,480, 2,980, 2,950, 1,750, 1,440, 1,350, 1,210, 1,160, 1,100 1,010, 860; 840; 810, 780, 750; 700.

NMR Spectrum (CCl$_4$):
peaks at 1:46 ppm(s) (hydrogens of methyls); at 3.79 ppm(s) (hydrogens of COOCH$_3$); at 4.66 ppm(s) (hydrogen of —CHO.)

STEP B: (4S,5S) 2,2-dimethyl-1,3-dioxolane-4,5-diyl-3,3'-di[methyl-(E)-propenate]

26.6 ml of a 1.5M diisobutylaluminium hydride in toluene were slowly added at −78° C. under an inert atmosphere to a solution of 4.36 g of the product of Step A in 50 ml of toluene and after stirring at −78° C. for two hours, a solution of sodium diethylphosphonate in dimethoxyethane was added dropwise. The mixture returned to room temperature and was stirred at 20° C. for 4 hours. 20 ml of water were added and the mixture was extracted with ether. The organic phase was dried and evaporated to dryness under reduced pressure. The 4.7 g of residue were chromatographed over silica and eluted with a 9–1 hexane-ethyl acetate mixture to obtain 2.3 g of the expected product with a specific rotation of $[\alpha]_D = -70.2°$ (c=6 mg/ml of CHCl$_3$).

The sodium diethylphosphonate solution was prepared by suspending 1.4 g of sodium hydride in 20 ml of dimethoxyethane at 0° C. under an inert atmosphere and then a solution of 9.45 g of methyl diethylphosphono acetate in 50 ml of dimethoxyethane was added and the mixture was stirred at 20° C. for 30 minutes.

STEP C: [(4S,5S) 2,2-dimethyl-1,3-dioxolane-4,5-diyl]-3,3'-di-[methyl 2,2-dimethyl-1R,3R-cyclopropane-carboxylate]

A solution of n-butyllithium in hexane was added to a suspension of isopropyltriphenylphosphonium iodide in tetrahydrofuran to obtain a solution of 12.5×10$^{-3}$M of triphenylisopropylidene phosphorane in tetrahydrofuran and 20 ml of the solution were added to a solution of 1.35 g of the product of Step B in 25 ml of tetrahydrofuran. After stirring at 0° C. for one hour and then at room temperature for one hour, the mixture was diluted with 10 ml of water and was extracted with ether. The extract was dried and evaporated to dryness under reduced pressure. The residue was chromatographed over silica to obtain the expected product in a 50 to 60% yield which after crystallization from cyclohexane had a specific rotation of $[\alpha]_D = -55.5°$ (c=20.25 in CHCl$_3$).

STEP D: [(1S,2S) 1,2-dihydroxyethylene]-3,3'-di-[methyl 2,2-dimethyl-1R,3R-cyclopropane carboxylate]

5 ml of an aqueous solution of 2N perchloric acid were added to a solution of 180 mg of the product of Step C in 4 ml of tetrahydrofuran and after stirring for 8 hours at 20° C., the mixture was neutralized with aqueous saturated sodium bicarbonate solution. The mixture was extracted with ether and the ether phase was dried and evaporated to dryness under reduced pressure to obtain 160 mg of raw product with a specific rotation of $[\alpha]_D = -67.5°$ (13.96 CHCl$_3$) which was used as is for the next step.

STEP E: Methyl (1R,3R) 2,2-dimethyl-3-formyl-cyclopropane carboxylate

The pH of a solution of 105 mg of the product of Step D in 4 ml of methanol was adjusted to 7 by addition of 2 ml of phosphate buffer and then 107 mg of sodium periodate were added all at once. The mixture was stirred at room temperature for 30 minutes and then was filtered. The filtrate was washed with ether and was evaporated to dryness under reduced pressure. The residue was taken up in ether and the solution was washed with water, dried and evaporated to dryness under reduced pressure. The 82 mg of residue were chromatographed on silica and eluted with a 7–3 pentane-ether mixture to obtain 72 mg of the expected product with a specific rotation of $[\alpha]_D = +18.85°$ (18.25 acetone).

EXAMPLE 2

Methyl (1S,3S) 2,2-dimethyl-3-formyl-cyclopropane-carboxylate

STEP A: [(4S,5S) 2,2-dimethyl 1,3-dioxolane-4,5-diyl]-3,3'-di-[methyl 2,2-dimethyl-1S,3S-cyclopropane carboxylate]

A solution of lithium diisopropylamide [obtained by reacting 0.325 g of diisopropylamine in 5 ml of dimethoxyethane and 2.1 ml of 1.55M of n-butyllithium in hexane for 15 minutes at −78° C.] was added at −78° C. under an inert atmosphere to a mixture of 0.915 g of isopropyldiphenylsulfonium tetrafluoroborate, 0.255 g of anhydrous dichloromethane and 12 ml of anhydrous dimethoxyethane and after stirring the mixture at −78° C. for 15 minutes, a solution of 0.27 g of the diester of Step B of Example 1 in 2 ml of dimethoxyethane was added. The mixture was stirred at −78° C. for 15 minutes and then for 45 minutes at −65° to −50° C. and was then heated for 15 minutes. 5 ml of water were added to the mixture and the organic phase was diluted with ether. The decanted organic phase was washed with water, dried and evaporated to dryness under reduced pressure and the 0.75 g of residue was chromatographed over silica. Elution with a 3–1 pentane-ether mixture yielded 0.29 g of the expected product melting at 136°–137° C. and having a specific rotation of $[\alpha]_D = -24.7°$ (c=16.6 mg/ml of chloroform).

NMR Spectrum (CDCl$_3$):
δ=1–1.6 (m with 1 to 1.2; 1.24 and 1.35 22H, CH$_3$ and cyclopropane H), 3.2–3.44 (m, 2H, H of dioxolane), 3.6 (s, 6H, COOCH$_3$)

STEP B: [(1S,2S) 1,2-dihydroxy-ethylene] 3,3'-di-[methyl-2,2-dimethyl 1S,3S-cyclopropane carboxylate]

Using the procedure of Step D of Example 1, 0.29 g of the product of Step A was reacted to obtain the raw expected product which was used as is for the next step.

STEP C: Methyl (1S,3S) 2,2-dimethyl-3-formyl-cyclopropane carboxylate

Using the procedure of Step E of Example 1, 0.31 g of the product of Step B were reacted with 0.32 g of sodium periodate and after filtration, washing with ether and evaporation to dryness, the residue was chromatographed on silica. Elution with a 2-8 ether-pentane mixture yielded 0.21 g of the expected product with a specific rotation of $[\alpha]_D = -18°$ (c=25.5 mg/ml of acetone).

EXAMPLE 3

Methyl (1R,3S) 2,2-dimethyl-3-formyl-cyclopropane-carboxylate

STEP A: (4S,5S) 2,2-dimethyl-1,3-dioxolane-4,5-diyl-3,3'-di[methyl (Z) propenate]

13.5 ml of a solution of a 1.5M of diisobutylaluminium hydride in toluene were slowly added at $-78°$ C. under an inert atmosphere to a solution of 2.18 g of the product of Step A of Example 1 in 50 ml of toluene and the mixture was stirred at $-78°$ C. for 2 hours. Then, a solution of 8.35 g of methyltriphenylphosphoranilidene acetate in 150 ml of methanol was added dropwise and the mixture was allowed to return to room temperature. The mixture was stirred at 20° C. for 3 hours and 50 ml of water were added. The methanol was distilled under reduced pressure and the mixture was extracted with ether. The organic phase was dried and evaporated to dryness under reduced pressure. 250 ml of pentane were added to the residue and the mixture was filtered. The filtrate was evaporated to dryness under reduced pressure to obtain 2.5 g of residue which was chromatographed over silica. Elution with a 7-3 pentane-ether mixture yielded 1.5 g of the expected product melting at 51°–52° C.

Analysis: $C_{13}H_{18}O_6$. Calculated: % C 57.8, % H 6.70. Found: % C 57.95, % H 6.70.

STEP B: [(4S,5S) 2,2-dimethyl-1,3-dioxolane-4,5-diyl]-3,3'-di-[methyl (1R,3S) 2,2-dimethyl-cyclopropane carboxylate]

Using the procedure of Step A of Example 2, 0.27 g of the product of Step A were reacted to obtain 0.24 g of the expected product melting at 97°–98° C. and having a specific rotation of $[\alpha]_D = -10.1°$ (c=5.6 mg/ml of CHCl$_3$).

NMR Spectrum (CDCl$_3$):

δ=0.9–1.6 (m with 3s to 1.16; 1.25 and 1.36, 22H, (CH$_3$)$_2$C and cyclopropane H); 3.56 (s, 6H, COOCH$_3$); 4.1–4.35 (m, 2H, CHO).

STEP C: [(1S, 2S) 1,2-dihydroxyethylene]-3,3'-di-[methyl (1R,3S) 2,2-dimethyl-cyclopropane-carboxylate]

Using the procedure of Step D of Example 1, 0.24 g of the product of Step B were reacted to obtain the raw expected product which was used as is for the next step.

STEP D: Methyl (1R,3S) 2,2-dimethyl-3-formyl-cyclopropane carboxylate

Using the procedure of Step E of Example 1, 0.31 g of the product of Step C were reacted with 0.32 g of sodium periodate to obtain 0.19 g of the expected product with a specific rotation of $[\alpha]_D = -73.2°$ (c=15.5 mg/ml of acetone).

Various modifications of the process of the invention may be made without departing from the spirit or scope thereof and it is to be understood that the invention is intended to be limited only as defined in the appended claims.

Col.   Line 19     50 to 60    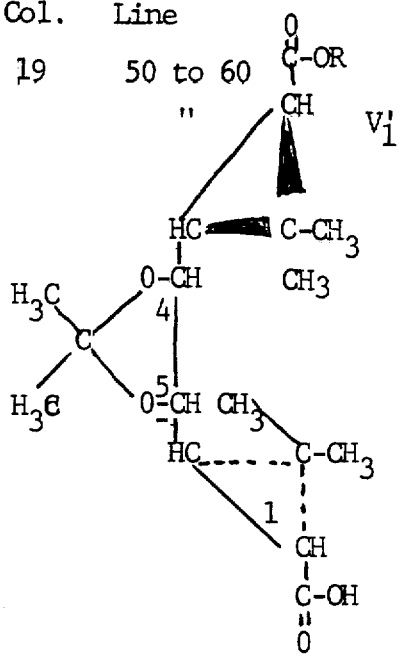    should be    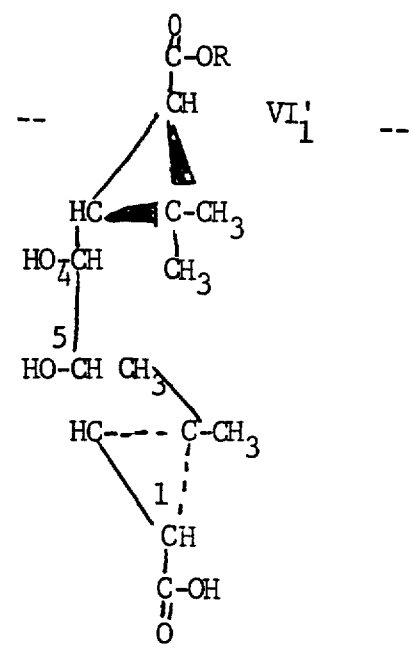

What we claim is:

1. A process for the preparation of racemates or optically active isomers of a compound of the formula

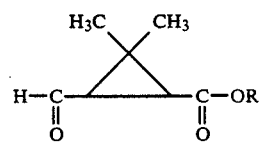

with cis or trans structures wherein R is selected from the group consisting of hydrogen, alkyl of 1 to 4 carbon atoms and aryl of 6 to 12 carbon atoms comprising reacting a diester of the formula

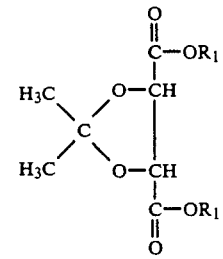

in racemic form or as resolved isomers wherein $R_1$ is selected from the group consisting of alkyl of 1 to 4 carbon atoms, aryl of 6 to 12 carbon atoms and aralkyl of 7 to 8 carbon atoms with a reducing agent to obtain a precursor of a compound of the formula

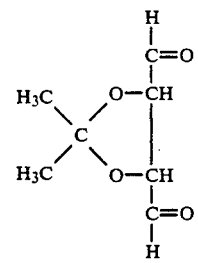

reacting the latter with a reagent of the formula

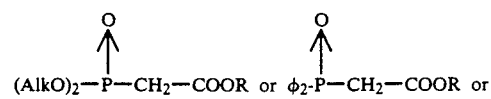

wherein R has the above definition, Alk is alkyl of 1 to 4 carbon atoms and φ is phenyl to obtain a compound of the formula

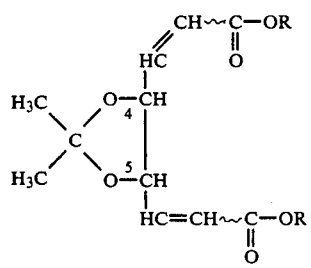

IV wherein R is as defined above and the wavy lines indicate the cis or trans configuration, reacting the latter with a gemdimethyl cyclopropanation reagent of the formula

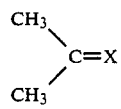

wherein X is P(Ar)₃, S(Ar)₂, or

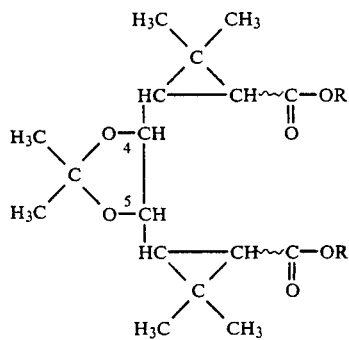

V

Ar is phenyl and R₂ is hydrogen or alkyl of 1 to 4 carbon atoms to obtain a compound of the formula

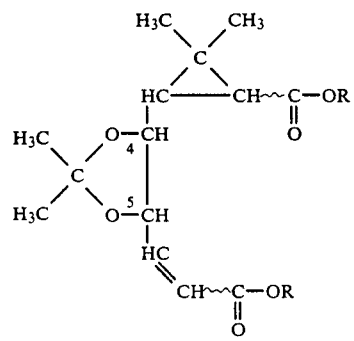

Va or a compound of the formula

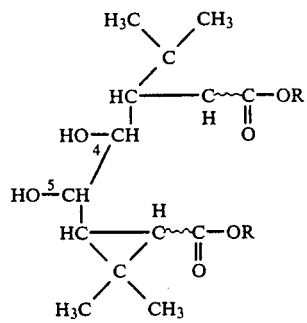

VI or

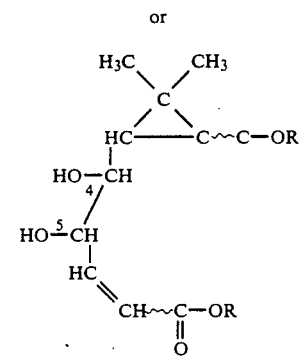

VIa wherein R and the wavy lines have the above definitions, optionally reacting the latter with a gem-dimethyl cyclopropanation agent to obtain the compound of formula V, the product of formula V or Va is either subjected to hydrolysis of the dioxolane group to obtain a compound respectively of the formula

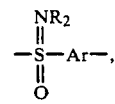

wherein R and the wavy lines have the above definitions and then cleaving the 4,5-bond with an oxidizing agent to obtain a compound of formula I or simultaneously hydrolyzing the dioxolane group and cleaving the 4,5-bond with an oxidizing agent to obtain the compound of formula I.

2. The process of claim 1 for the preparation of racemic or optically active isomers of a compound of the formula

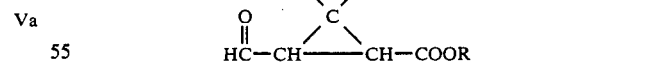

I$_B$ with a trans structure wherein R has the definition of claim 1 comprising reacting the compound of formula II in racemic or resolved isomeric form with a reducing agent to obtain a precursor of the compound of formula III with the corresponding isomeric structure and reacting the latter with a compound of the formula

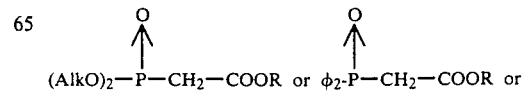

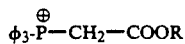

wherein R has the definition of claim 1, Alk is alkyl of 1 to 4 carbon atoms and φ is phenyl to obtain a compound of the formula

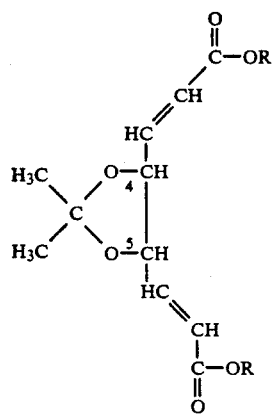   IV' with the geometry of the double bond being trans, subjecting the latter to a gem-dimethyl cyclopropanation agent of the formula

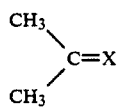

wherein X is P(Ar)₃, S(Ar)₂ or

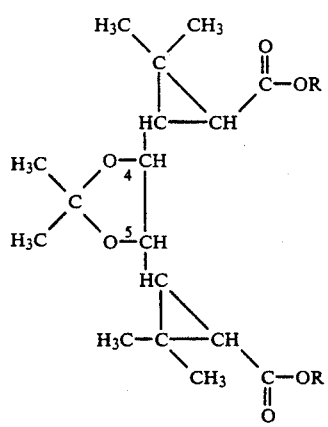   V'

Ar is phenyl and R₂ is hydrogen or alkyl of 1 to 4 carbon atoms to obtain a compound of the formula

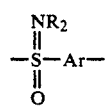

wherein the cyclopropane ring configuration is trans and either hydrolyzing the dioxolane of the latter to obtain a compound of the formula

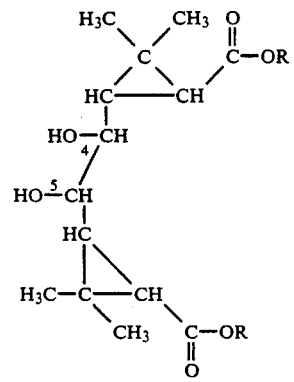   VI' wherein the cyclopropane ring configuration is trans and cleaving the 4,5-bond with an oxidizing agent to obtain a compound of formual I_A or simultaneously hydrolyzing the dioxolane and cleaving the 4,5-bond with an oxidizing agent to obtain a compound of formula I_A.

3. The process of claim 2 wherein the compound has 1R, trans configuration comprising reacting a compound of the formula

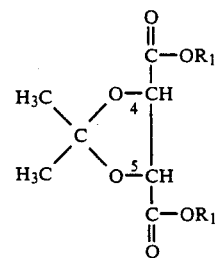   II₁ of (4R, 5R) configuration and R₁ is selected from the group consisting of alkyl of 1 to 4 carbon atoms, aryl of 6 to 12 carbon atoms and aralkyl of 7 to 8 carbon atoms with diisobutylaluminium hydride to obtain a corresponding precursor of a compound of the formula

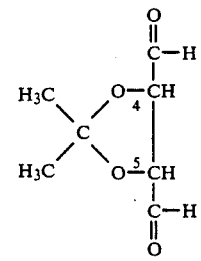   III₁ with (4R, 5R) configuration, reacting the latter with a compound of the formula

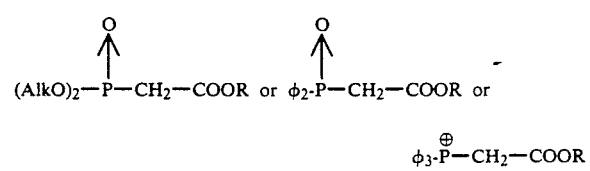

wherein R has the definition of claim 2, Alk is alkyl of 1 to 4 carbon atoms and φ is phenyl to obtain a compound of the formula

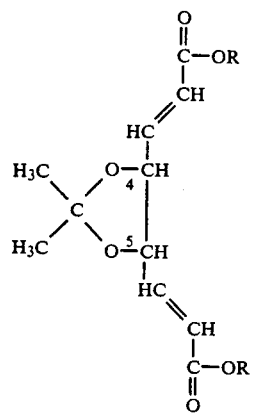

with (4S, 5S) configuration and the double bond geometry is trans, reacting the latter with isopropylidine triphenylphosphorane to obtain a compound of the formula

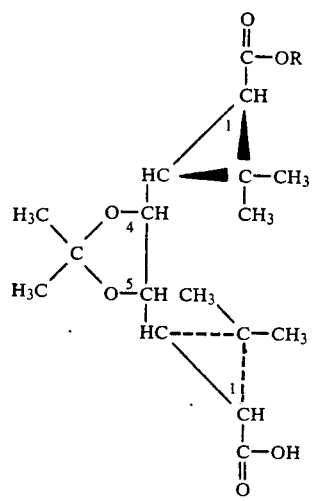

with the (4S, 5S) configuration and (1R, trans) configuration on the cyclopropanic ring and either subjecting the latter to hydrolysis of the dioxolane to obtain a compound of the formula

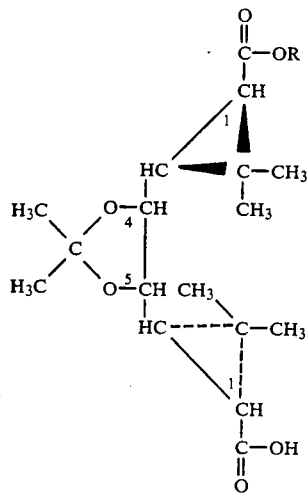

with (4S, 5S) configuration and (1R, trans) configuration on the cyclopropane ring and cleaving the 4,5-bond with an oxidizing agent with an oxidation agent to obtain the compound of formula $I_A$ with a (1R, trans) configuration or simultaneously hydrolyzing the dioxolane group and cleaving the 4,5-bond with an oxidizing agent to form a compound of Formula $I_A$ with a (1R, trans) configuration.

4. The process of claim 1 for the preparation of a reacemate or optical isomer of a compound of the formula

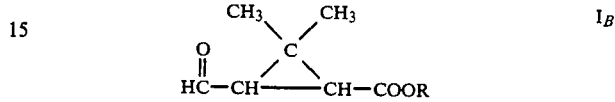

of cis structure and R has the definition of claim 1 comprising reacting a compound of formula II in racemic or resolved isomeric form with a reducing agent to obtain a precursor of a compound of formula III with a corresponding isomeric structure, reacting the latter with a compound of the structure

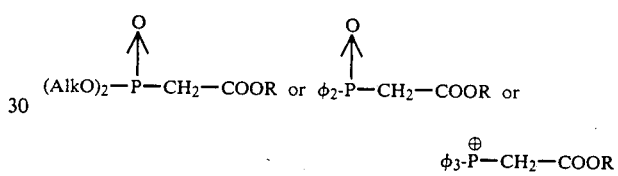

wherein R has the definition of claim 1, Alk is alkyl of 1 to 4 carbon atoms and $\phi$ is phenyl to obtain a compound of the formula

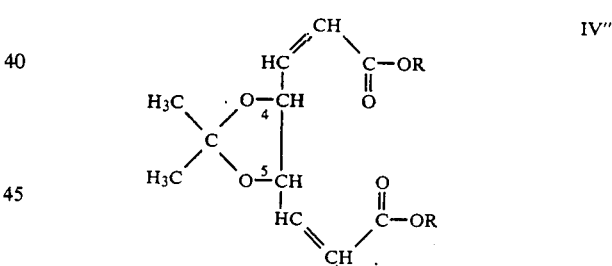

wherein the double bond has cis geometry, reacting the latter with isopropylidene diphenylsulfurane to obtain a compound of the formula

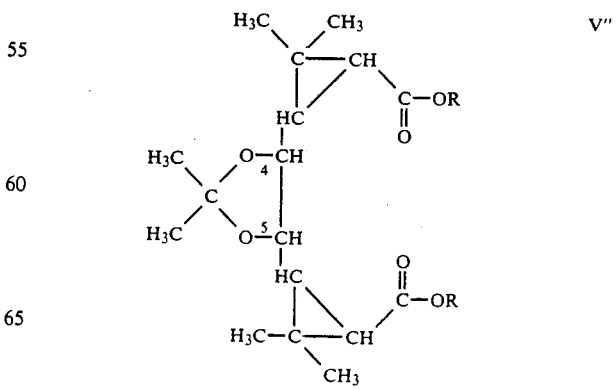

with a cis configuration of the cyclopropane ring and either hydrolyzing the dioxolane group to obtain a compound of the formula

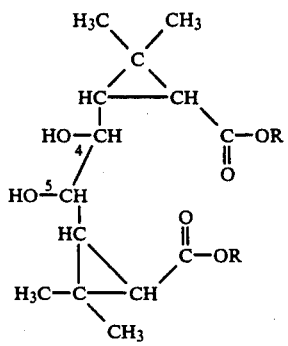   VI'' of cis configuration and cleaving the 4,5-bond with an oxidizing agent to obtain the corresponding compound of formula $I_B$ or simultaneously hydrolyzing the dioxolane group and cleaving the 4,5-bond with an oxidizing agent to obtain a compound of formula $I_B$.

5. The process of claim 4 for the preparation of a compound of formula $I_B$ with (1R, cis) configuration comprising reacting a compound of the formula

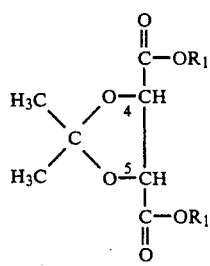   II₁ with (4R, 5R) configuration and R₁ has the definition of claim 4 with diisobutylaluminum hydride to obtain a corresponding precursor of a compound of the formula

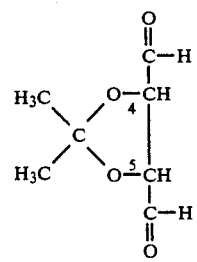   III₁ with (4R, 5R) configuration, reacting the latter with a compound of the formula

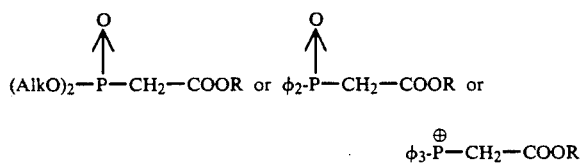

wherein R has the definition of claim 4, Alk is alkyl of 1 to 4 carbon atoms and φ is phenyl to obtain a compound of the formula

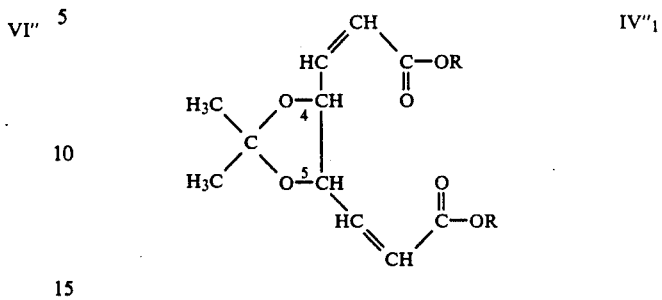   IV''₁ with (4S, 5S) configuration and the double bond geometry is cis, reacting the latter with isopropylidene diphenylsulfurane to obtain a compound of the formula

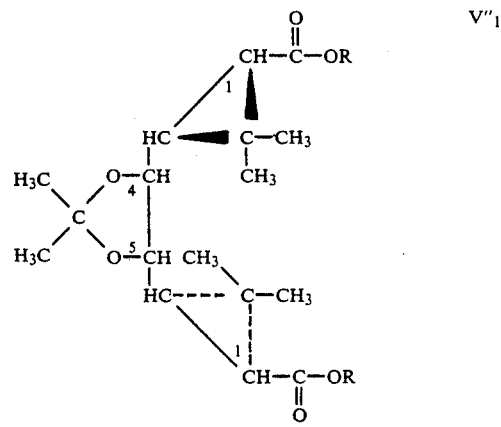   V''₁ with (4S, 5S) configuration and (1R, cis) configuration on the cyclopropane ring and either hydrolyzing the dioxolane group to obtain a compound of the formula

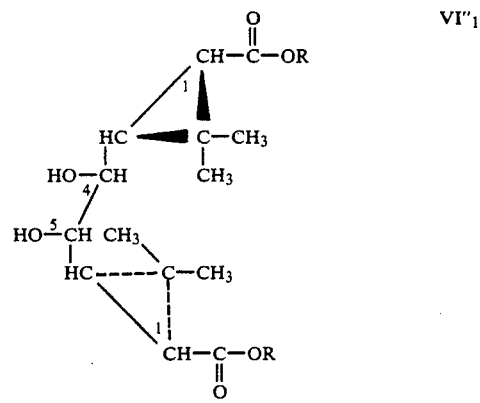   VI''₁ with (4S, 5S) configuration and (1R, cis) configuration on the cyclopropane ring and cleaving the 4,5-bond with an oxidizing agent with an oxidizing agent to obtain a compound of formula $I_B$ with (1R, cis) configuration or simultaneously hydrolyzing the dioxolane group and cleaving the 4,5-bond with an oxidizing agent to obtain a compound of formula $I_B$ with (1R, cis) configuration.

* * * * *

UNITED STATES PATENT AND TRADEMARK OFFICE
CERTIFICATE OF CORRECTION

PATENT NO. : 4,996,349
DATED : Feb. 26, 1991

Page 1 of 4

INVENTOR(S) : ALAIN KRIEF and WILLY DUMONT

It is certified that error appears in the above-identified patent and that said Letters Patent is hereby corrected as shown below:

Col.   Line
2      8       After "phosphorus" insert --residue--
9      55

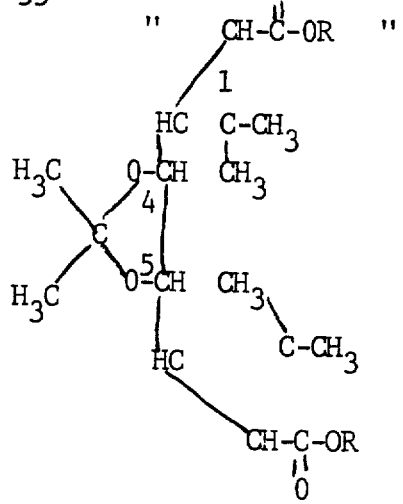 should be 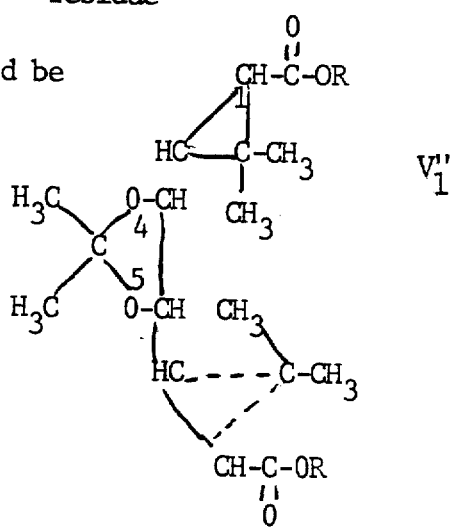

Signed and Sealed this

Fourteenth Day of September, 1993

*Attest:*

BRUCE LEHMAN

*Attesting Officer*   Commissioner of Patents and Trademarks

UNITED STATES PATENT AND TRADEMARK OFFICE
CERTIFICATE OF CORRECTION

PATENT NO. : 4,996,349
DATED : Feb. 26, 1991
INVENTOR(S) : ALAIN KRIEF and WILLY DUMONT It is certified that error appears in the above-identified patent and that said Letters Patent is hereby corrected as shown below:

| Col. | Line | |
|---|---|---|
| 15 | 30 | After wherein X is $P(Ar)_3$, $S(Ar)_2$, or insert-- $\overset{NR_2}{\underset{O}{\overset{\|}{\underset{\|}{S}}}}-Ar$ --Ar is phenyl and $R_2$ sis hydrogen or alkyl of 1 to 4 carbon atoms to obtain a compound of the formula-- |
| 15 | 47&48 | "delete Ar is phenyl and $R_2$ is hydrogen or alkyl of 1 to 4 carbon atoms to obtain a compound of the formula" |
| 15 | 55 | 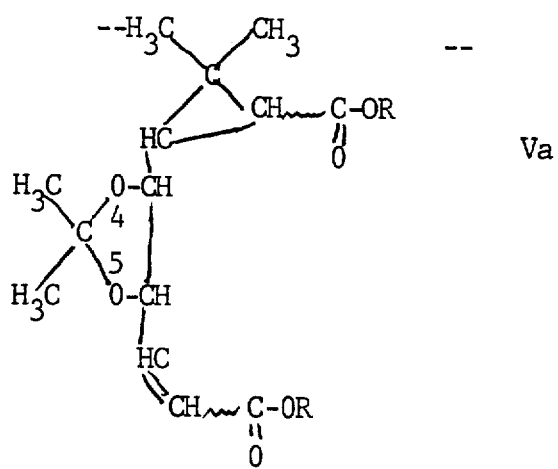 Va  should be after --or a compound of the formula-- |

UNITED STATES PATENT AND TRADEMARK OFFICE
CERTIFICATE OF CORRECTION

PATENT NO. : 4,996,349

DATED : Feb. 26, 1991

Page 3 of 4

INVENTOR(S) : ALAIN KRIEF and WILLY DUMONT

It is certified that error appears in the above-identified patent and that said Letters Patent is hereby corrected as shown below:

| Col. | Line |  |
|---|---|---|
| 16 | 30 to 35 | --wherein R and the wavy lines have the above definitions, optionally reacting the reacting the latter with a gem-dimethyl cyclopropanation agent to obtain the compound of formula V, the product of formula V or Va is either subjected to hydrolysis of the dioxolane group to obtain a compound respectively of the formula-- should be before the formula VI |
| 16 | 36 to 40 | $$\begin{array}{c}--NR_2--\\ \|\\ S-Ar-,\\ \|\\ O\end{array}$$ should be in Col. 15 after --wherein X is $P(Ar)_3$, $S(Ar)_2$, or -- |
| 16 | 36 to 40 | $$\begin{array}{c}--NR_2\\ \|\\ S-Ar-,\\ \|\\ O\end{array}$$ delete from this col. |
| 17 | 55 | --Ar is phenyl and $R_2$ is hydrogen or alkyl of 1 to 4 carbon carbon atoms to obtain a compound of the formula-- should be before formula V' |
| 17 | 60 | Delete $\begin{array}{c}NR_2\\ \|\\ S-Ar-\\ \|\\ O\end{array}$ |

UNITED STATES PATENT AND TRADEMARK OFFICE
CERTIFICATE OF CORRECTION

PATENT NO. : 4,996,349

DATED : Feb. 26, 1991

INVENTOR(S) : ALAIN KRIEF and WILLY DUMONT

It is certified that error appears in the above-identified patent and that said Letters Patent is hereby corrected as shown below: